(12) United States Patent
James

(10) Patent No.: US 8,167,857 B2
(45) Date of Patent: May 1, 2012

(54) OSTOMY SUCTION SYSTEM

(76) Inventor: Margarita James, Danbury, CT (US)

( * ) Notice: Subject to any disclaimer, the term of this patent is extended or adjusted under 35 U.S.C. 154(b) by 680 days.

(21) Appl. No.: 12/341,269

(22) Filed: Dec. 22, 2008

(65) Prior Publication Data
US 2010/0160875 A1    Jun. 24, 2010

(51) Int. Cl.
A61M 1/00    (2006.01)
A61F 5/44    (2006.01)

(52) U.S. Cl. ........ 604/319; 604/317; 604/322; 604/334; 604/540; 604/541; 604/543

(58) Field of Classification Search .................. 604/317, 604/319, 322, 540, 334, 541, 543
See application file for complete search history.

(56) References Cited

U.S. PATENT DOCUMENTS

| | | | |
|---|---|---|---|
| 3,830,235 A | 8/1974 | Marsan | |
| 3,881,486 A * | 5/1975 | Fenton | 604/335 |
| 4,588,402 A * | 5/1986 | Igari et al. | 604/408 |
| 4,692,159 A | 9/1987 | Kuzemchak | |
| 4,772,260 A * | 9/1988 | Heyden | 604/45 |
| 4,941,869 A | 7/1990 | D'Amico | |
| 5,616,138 A * | 4/1997 | Propp | 604/317 |
| 5,658,267 A | 8/1997 | Colacello et al. | |
| 5,690,621 A | 11/1997 | Canela | |
| 5,709,236 A | 1/1998 | Rodriguez | |
| 6,050,982 A | 4/2000 | Wheeler | |
| 6,132,408 A * | 10/2000 | Lutz | 604/335 |
| 6,582,410 B1 | 6/2003 | Rutman | |
| 6,785,916 B2 * | 9/2004 | Tanaka | 4/455 |
| 6,840,923 B1 | 1/2005 | Lapcevic | |
| 7,699,831 B2 * | 4/2010 | Bengtson et al. | 604/541 |
| 7,749,205 B2 * | 7/2010 | Tazoe et al. | 604/320 |
| 2007/0010798 A1 * | 1/2007 | Stoller et al. | 604/544 |

* cited by examiner

Primary Examiner — Tatyana Zalukaeva
Assistant Examiner — Ginger T Chapman

(57) ABSTRACT

An ostomy drainage system comprising an ostomy bag or pouch connected by tubes to a container which is connected via tubes to a vacuum device whereby the contents of the ostomy bag can be suctioned into the container to prevent frequent changing of the ostomy bag thereby improving sanitation and convenience for ostomy patients.

14 Claims, 1 Drawing Sheet

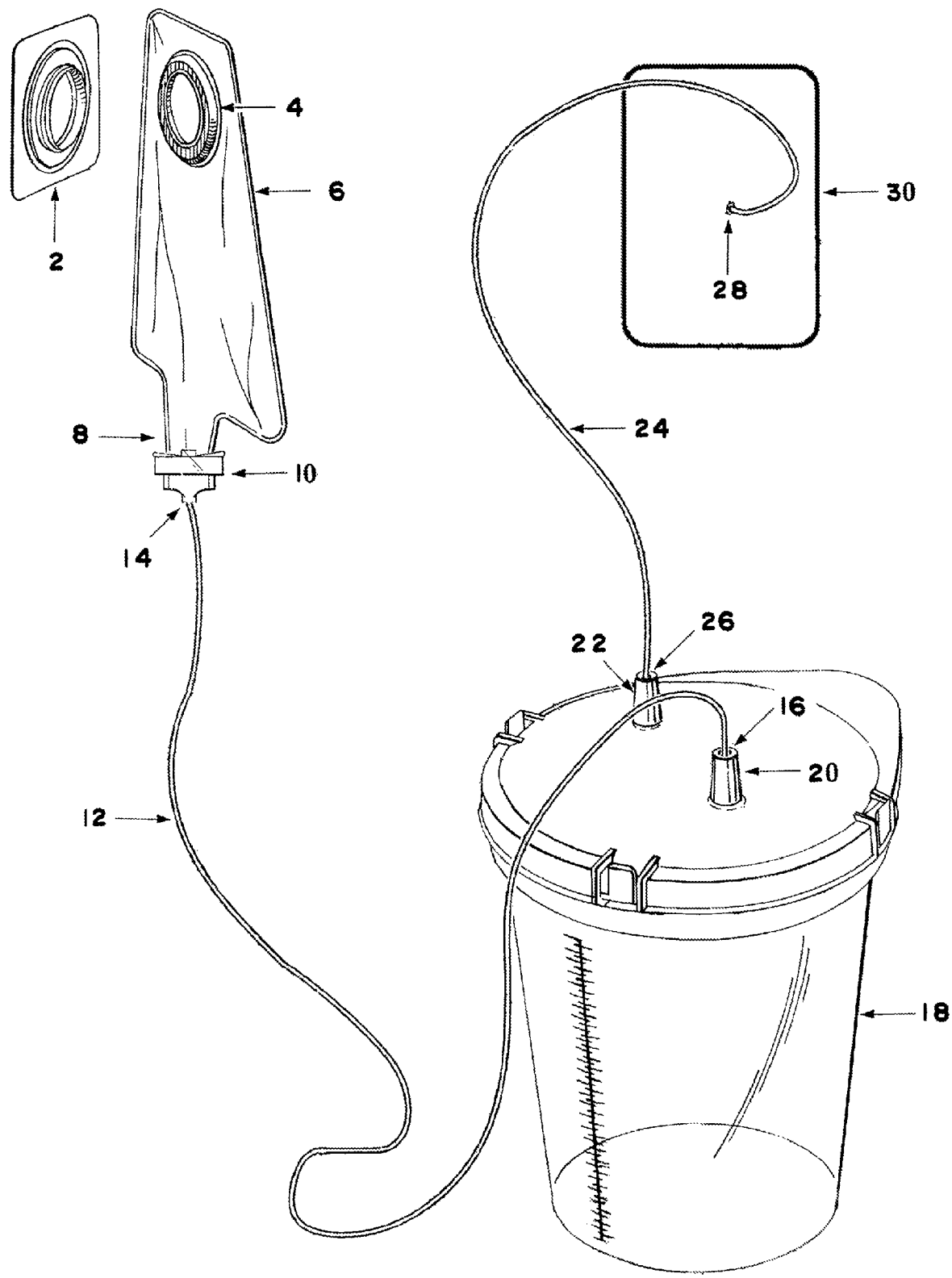

OSTOMY SUCTION SYSTEM

FIELD OF THE INVENTION

The present invention relates to ostomy devices and more particularly pertains to a new ostomy suction system.

BACKGROUND OF THE INVENTION

An ostomy is a surgical procedure creating an opening in the body for the discharge of body wastes. Certain diseases of the bowel may involve removing parts of the small and/or large intestine. This creates a need for an alternate way to remove feces or waste from the body. An opening is surgically created in the abdomen for body wastes to pass through and this opening is called a stoma. Different types of ostomy are performed depending on how much and what parts of the intestines are removed.

The two most common types of ostomies are colostomy and ileostomy. A colostomy is when a small portion of the colon (large intestine) is brought to the surface of the abdominal wall to allow stools or waste to be eliminated. An ileostomy is an opening created in the small intestine to bypass the colon for stool elimination. The end of the ileum, which is the lowest part of the small intestine, is brought through the abdominal wall to form a stoma.

In order to remove the waste in standard ostomy care, an adhesive is attached to the skin around the stoma, and a colostomy bag is snapped onto a plastic ring on the adhesive. Typically the bag is replaced when it is ⅓ full about 10 times a day, because if it gets too full, waste can leak between the adhesive and skin. In addition, if the bag is too full, it will spill when the bag needs emptying or replacing.

Replacing of the bag causes stress on the adhesive, leading to its frequent changing. It is important to change the adhesive as infrequently as possible, because frequent changing of the adhesive causes skin tears, which are hard to heal and are prone to infection. If bacteria contacts with the skin tears, healing of the wounds are even more difficult and can be life threatening. With existing products, liquid stool or waste almost always leaks between the adhesive and patient's body. When this occurs, the adhesive must be removed because of sanitary reasons and loss of adherence, making skin tears inevitable. This is unsanitary and unpleasant for the patients.

One solution to limit the changing of the bag and the stress it causes to the adhesive is to use gravity to drain the pouch. This typically involves having an open end to the bag, sealed by a clamp or device, which can be opened. Emptying the bag involves releasing the clamp and allowing the waste to empty into a toilet or other receptacle. This is often messy, unsanitary and unpleasant for the patient. It also puts stress on the adhesive and is especially inconvenient if it is difficult or impossible for the patient to get out of bed.

Another solution to frequent changing of the bag is to use gravity to drain the pouch into a bottle. However, the problem with this method is that the tubes leading from the bag often get clogged with fecal matter resulting in fecal matter build up and requiring frequent changing of the ostomy bag and adhesive.

Elaborate hand pumps, bottles, stoma plugs and irrigation systems have also been disclosed in patent applications. However, these are expensive, complicated and elaborate systems. In most cases, they can be dangerous and difficult to use. This is why they never made it to market.

Thus, there is a need for a new ostomy drainage system, limiting the need for frequent changing of the ostomy bag, involving more sanitary conditions and more convenience for the patient.

SUMMARY OF THE INVENTION

The general purpose of the present invention is to provide a new ostomy drainage system, which generally improves on many of the disadvantages of the ostomy devices mentioned above. To attain this, the present invention generally comprises an ostomy bag (or pouch) connected by tubes to a container. The container is then connected via tubes to a vacuum device whereby the contents of the ostomy bag can be suctioned into the container. This prevents the frequent changing of the ostomy bag thereby improving upon the sanitation and convenience of the ostomy patients.

BRIEF DESCRIPTION OF THE DRAWINGS

FIG. 1 is general schematic perspective of the new ostomy suction system of the present invention.

DETAILED DESCRIPTION OF THE INVENTION

The present invention is an ostomy suction system involving suction or vacuum comprising: a stoma engaging device for engaging the stoma of a user; an ostomy bag, said ostomy bag having a first aperture and a second aperture, wherein said first aperture being adapted to be coupled to said stoma engaging device such that contents from the stoma may enter said first aperture in said ostomy bag; a first tubular member, said tubular member being elongate and having an open first end and an open second end, said tubular member being generally hollow, and said first end being adapted to be coupled to said second aperture of said ostomy bag; a container, said container having a first aperture and second aperture; said first aperture being adapted to be coupled to said open second end of said first tubular member; a second tubular member, said tubular member being elongate and having an open first end and an open second end, said tubular member being generally hollow, and said first end being adapted to be coupled to said second aperture of said container; a vacuum device; wherein said vacuum device generates a vacuum and is adapted to be coupled to said open second end of said second tubular member.

The stoma engaging device of the present invention is a device that connects the stoma to the ostomy bag or pouch. It can be a separate individual component removable, connected or coupled to the ostomy bag or it can be a permanent component fixed to the bag. The stoma engaging device generally has an adhesive such that the stoma engaging device can adhere to the skin surrounding the stoma to prevent leakage of the waste. In some instances, the stoma engaging device does not have an adhesive and an adhesive composition must be added to the stoma engaging device prior to contact with the stoma.

The ostomy bag or pouch can be made of any material, preferably those used in the ostomy industry. It is generally made of a soft plastic material, whereby the grade of plastic films used to make the bags typically meet several criteria such as impermeability, mechanical strength, seam strength, gas/odor barrier protection and flexibility. The ostomy bag may be any type of ostomy-bag such as a colostomy or ileostomy bag. Examples of the types of ostomy bags and stoma engaging devices that may be used in this invention are those made by Hollister Inc, Convatech Inc. and Coloplast Corp.

A tube or tubular member (e.g., hose) connects the ostomy bag to a container that will collect the waste. This waste tube can be made of any material, but preferably is made of a generally flexible material such as plastic so that it can be bent in different directions. This is preferable since the waste tubing or waste container may have to be moved due to the needs of the patient. However, it should not bend enough to put a crimp in the waste tube that will cause the waste material to be blocked. One skilled in the plastic arts would be able to choose a suitable plastic material for the waste tube connecting the ostomy bag to the container.

The connection of the waste tube to the ostomy bag may be any suitable connection. The waste tube may be permanently affixed to the ostomy bag or have a removable connection, such as a flange or snap connector. The ostomy bag may contain a valve at or near the second aperture where the waste tube connects to ostomy bag. The valve can be closed and the waste tube removed for maintenance or cleaning. The waste tube should be connected in such in a manner to prevent waste from spilling from this connection.

Likewise, the connection from the waste tube to the container (waste container) may be any suitable connection. Preferably, it is a removable connection whereby the waste container may be emptied without disturbing the ostomy bag. The waste tube connection to the waste container may also contain a valve whereby the valve can be closed and the tube removed for maintenance, cleaning or removal of the waste container. The inner diameter of the waste tube should be sized such that waste can easily flow from the ostomy bag to the waste container. Preferably, the inner diameter of the waste tube can range from about 0.1 inches to about 3 inches, or about 0.2 inches to about 2 inches or about 0.25 inch to about 1 inch.

The waste container may be made of any suitable material such as metal, glass or plastic. It may be clear with graduated markings to determine how much waste has accumulated in a certain period of time or when to change it. The apertures of the waste container can be built into the waste container or may be separate from the waste container such as a cap having the aperture that may be removably coupled to the waste container.

The tube or tubular member (suction tube) from the waste container to the vacuum device may be made of any suitable material. It may be metal (e.g., copper) if it is preferable to make it a more permanent connection or from a generally flexible material such as a plastic material if it is desirable to move the waste container. The sizing of the tube should allow for a suction to be developed from the waste container to the ostomy bag such that waste material is drawn from the ostomy bag to the waste container.

The vacuum device may be any suitable device that generates a vacuum. Preferably, the vacuum device is a vacuum pump and more preferably a vacuum pump designed for medical systems (e.g., clean, quiet, etc). These types of medical system pumps are available commercially. Examples of vacuum pumps that may be used are rotary vane pump, diaphragm pump, liquid ring pump, piston pump, impeller pumps, scroll pump, linear pumps, screw pump, wankel pump, external vane pump or roots blower pump. The vacuum device may be operated constantly or intermittently.

In many hospitals or clinics, a vacuum device or system is already available and it is preferred that an existing vacuum device be used for this invention.

Preferably, the amount of vacuum in the ostomy drainage system of the present invention should be enough to gently pull the waste material from the ostomy bag, but not enough to exert too much vacuum on the stoma engaging device or the stoma itself. This may be accomplished by operating the vacuum device in such a manner to provide sufficient suction to pull the waste material from the ostomy bag into the waste container, but insufficient to suction contents from the stoma or collapse the ostomy bag.

There are many variables that would influence the amount of vacuum such as the size of tile vacuum pump, size of the waste container, length and size of the waste tubing and vacuum tubing, etc. One simple test that may be used and that does not require undue experimentation is to assemble the ostomy drainage system and apply a vacuum. Detach the waste tube from the ostomy bag, if possible, and place a finger over the open end of the tube to sense a vacuum. Next attach the tube to the ostomy bag and place a finger over the stoma engaging device opening to sense a vacuum. If the vacuum is noticeable, which may cause the ostomy bag to collapse or the adhesive of the stoma engaging device to fail, the vacuum should be reduced.

If the waste tube is not detachable from the ostomy bag, a vacuum should be pulled and the vacuum on the stoma engaging device should be checked using the procedure above. After temporary disengaging the vacuum, the ostomy drainage system should be connected to the patient. The vacuum should be engaged and the waste monitored to determine if it is being drawn into the waste container. If the vacuum is insufficient, it should be increased. This simple trial and error procedure may be used to determine the necessary vacuum and thus would not require undue experimentation.

The ostomy drainage system should be operated such that the contents of the waste container are not suctioned into the vacuum device. This may be accomplished by adjusting the vacuum. Another embodiment to accomplish this is to place the first aperture of the waste container that is connected to the ostomy bag and the second aperture of the waste container connected to the vacuum device is a positioned distal from each other such that it minimizes the probability that contents of waste container is suctioned into the vacuum device.

The waste container and vacuum device may be placed in any suitable location. Preferably, the vacuum device is placed in a room or chase outside of the patient's room to prevent contamination of the patient's room and reduce noise to the patient and staff. The vacuum device may be a device especially designed for the ostomy drainage system of the present invention or a device that is currently used in the hospital or clinic. The vacuum device may be used for only one ostomy drainage system or mutiple systems, including those not necessarily associated with ostomy, depending on the needs of the patient and hospital or clinic.

The waste container may be placed in the patient's room or in another room. Preferably, it is placed away from the patient such that medical personnel or staff can have access to the patient.

Reference is now made to FIG. 1, which describes an embodiment of the Ostomy suction system of the present invention.

The ostomy suction system generally comprises a stoma engaging device 2 for engaging a stoma of a user. An ostomy bag 6, has a first aperture 4 and a second aperture 8. The first aperture 4 being adapted to be coupled to the stoma engaging device 2 such that contents from the stoma may enter the first aperture 4 in the ostomy bag 6. The ostomy bag 6, may optionally also have a valve 10 at or near the second aperture 8.

A first tubular member 12 has an open first end 14 and an open second end 16, where the open first end 14 being adapted to be coupled to the second aperture 8 of the ostomy bag 6.

A waste container 18 has a first aperture 20 and second aperture 22 where the first aperture 20 being adapted to be coupled to the open second end 16 of the first tubular member 12.

A second tubular member 24 has an open first end 26 and an open second end 28, where the first open end 26 is adapted to be coupled to the second aperture 22 of the waste container 18.

A vacuum device 30 which generates a vacuum is adapted to be coupled to the open second end 28 of the second tubular member 24.

The invention described and claimed herein is not to be limited in scope by the specific examples and embodiments herein disclosed, since these examples and embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fail within the scope of the appended claims.

What is claimed is:

1. An ostomy drainage system comprising:
    a stoma engaging device for engaging a stoma of a user;
    an ostomy bag, said ostomy bag having a first aperture and a second aperture, wherein said first aperture being adapted to be coupled to said stoma engaging device such that contents from the stoma may enter said first aperture in said ostomy bag;
    a first tubular member, said tubular member being elongate and having an open first end and an open second end, said tubular member being generally hollow, and said first end being adapted to be coupled to said second aperture of said ostomy bag;
    a container, said container having a first aperture and second aperture; said first aperture being adapted to be coupled to said open second end of said first tubular member;
    a second tubular member, said tubular member being elongate and having an open first end and an open second end, said tubular member being generally hollow, and said first end being adapted to be coupled to said second aperture of said container;
    a vacuum device; wherein said vacuum device generates a vacuum and is adapted to be coupled to said open second end of said second tubular member.

2. The system of claim 1, wherein said vacuum device is a vacuum pump.

3. The system of claim 1, wherein said vacuum device is operated such that the amount of vacuum provided is sufficient to suction the contents from said ostomy bag into said container, but insufficient to suction contents from said stoma.

4. The system of claim 3, wherein said vacuum device is operated such that the contents of said container is not suctioned into said vacuum device.

5. The system of claim 3, wherein said first aperture and said second aperture of said container is positioned distal from each other such that it minimizes the probability that contents of said container is suctioned into said vacuum device.

6. The system of claim 2, wherein vacuum pump is a rotary vane pump, diaphragm pump, liquid ring pump, piston pump, impeller pumps, scroll pump, linear pumps, screw pump, wankel pump, external vane pump or roots blower pump, and wherein said vacuum pump is designed for medical system use.

7. The system of claim 1, wherein said first or second tubular member is generally flexible.

8. The system of claim 1, wherein said ostomy bag is a colostomy bag.

9. The system of claim 1, wherein said vacuum device configured to be used with is a vacuum system currently used in an existing hospital or clinic.

10. The system of claim 1, wherein said first aperture of said ostomy bag is adapted to be removably coupled to said stoma engaging device.

11. The system of claim 1, wherein said first aperture of said container is adapted to be removably coupled to said open second end of said first tubular member and wherein said first end of said second tubular member is adapted to be removably coupled to said second aperture of said container.

12. The system of claim 1, wherein said ostomy bag contains a valve at or near the second aperture of said ostomy bag.

13. The system of claim 11, wherein said first tubular member is removably coupled to said ostomy bag.

14. The system of claim 1, wherein said vacuum system is operated constantly or intermittently.

* * * * *